United States Patent [19]

Schäfer

[11] 4,039,884

[45] Aug. 2, 1977

[54] DISCHARGE LAMP FOR THE DISACTIVATION OF MICRO-ORGANISMS

[75] Inventor: Jürgen F. Schäfer, Niedermittlau, Germany

[73] Assignee: Original Hanau Quarzlampen, Hanau, Germany

[21] Appl. No.: 707,407

[22] Filed: July 21, 1976

[30] Foreign Application Priority Data

Aug. 11, 1975 Germany .............................. 2535816
May 7, 1976 Germany .............................. 2620251

[51] Int. Cl.² ............................................. H01J 61/12
[52] U.S. Cl. .................................... 313/225; 313/227; 313/228

[58] Field of Search ....................... 313/225, 228, 227; 250/373

[56] References Cited

U.S. PATENT DOCUMENTS 3,566,105  2/1971  Wiltrout et al. ..................... 250/373

Primary Examiner—Rudolph V. Rolinec
Assistant Examiner—Darwin R. Hostetter
Attorney, Agent, or Firm—Sughrue, Rothwell, Mion, Zinn and Macpeak

[57] ABSTRACT

There is disclosed a discharge lamp for deactivation of microorganisms having an emitted radiation suitable for such deactivation. The discharge lamp is a metal halide discharge lamp which contains antimony as a metal and iodine as the halogen.

10 Claims, 4 Drawing Figures

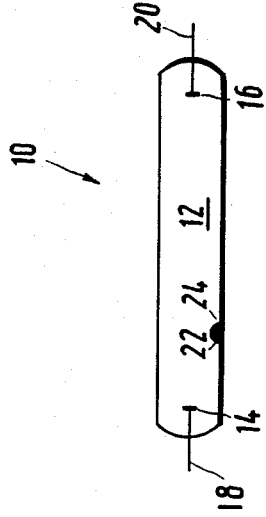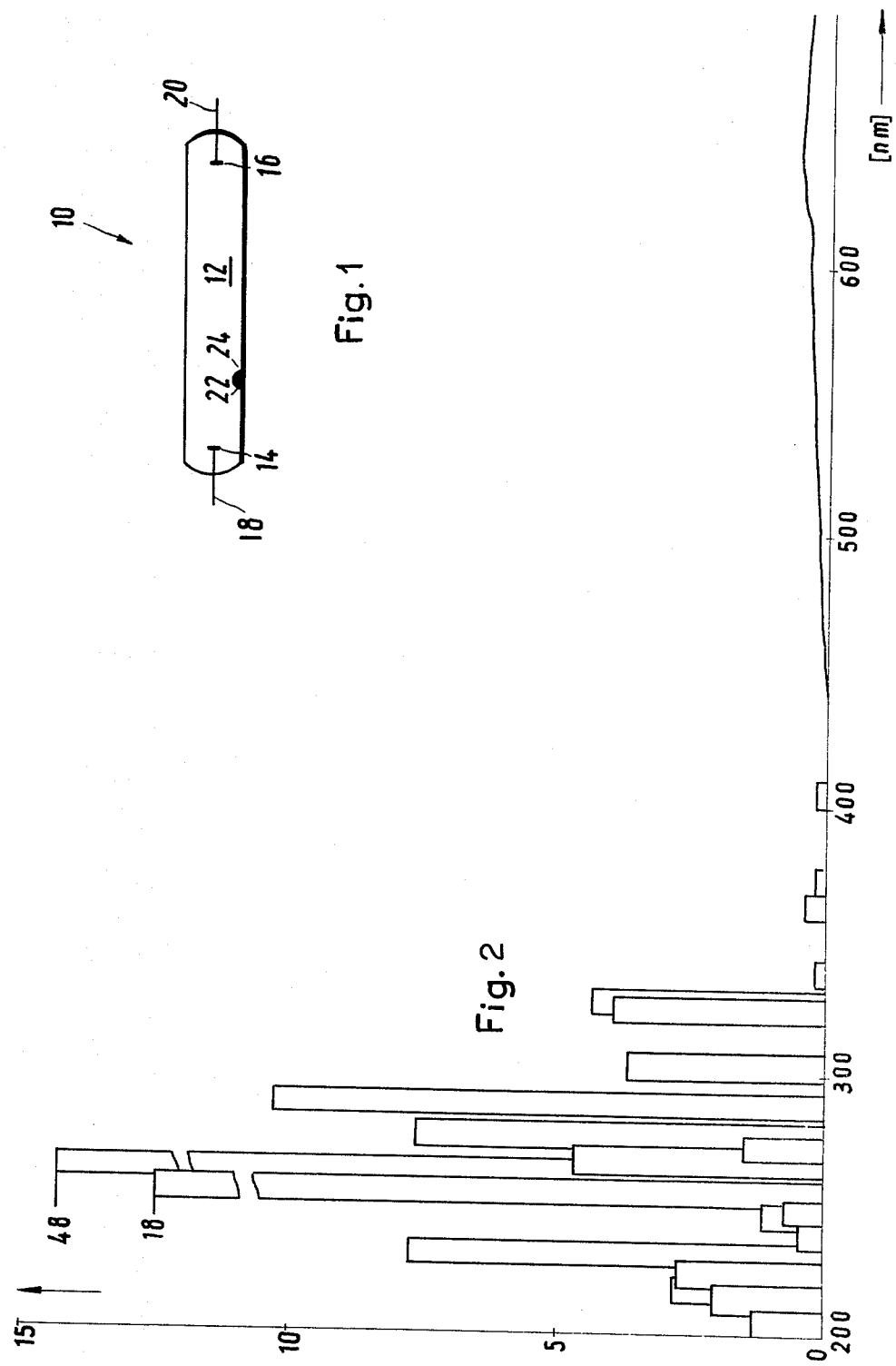

DISCHARGE LAMP FOR THE DISACTIVATION OF MICRO-ORGANISMS

BACKGROUND OF THE INVENTION

1. Field of the Invention

The invention relates to a discharge lamp for the disactivation of micro-organisms having an emitted radiation suitable for disactivation.

2. Prior Art

There are known discharge lamps being used for disactivation of micro-organisms in gases and fluids. In German specification No. 1 679 567 a room air purifying device is described that cleans the air by the effect of ultraviolet rays. As a source of ultraviolet rays one preferably used is a low pressure mercury burner. An electric room air deodorizing device with ultraviolet low pressure burners is disclosed in German disclosure 1 492 460.

Also, a room disinfecting device is disclosed in German registered design 7 314 612 using quartz lamps emitting an ultraviolet radiation for the formation of ozone, the wave length range of which not beng exactly given.

A device for the disinfection of water by means of immersion lamps in which a discharge lamp is being arranged, is shown in U.S. Pat. No. 3,566,105. The discharge lamp described therein concerns likewise a mercury discharge lamp.

Although the mercury discharge lamps described in the above mentioned arrangements are emitting radiations in the wave length range between 260 to 280 nm, corresponding to the wave length range for the optimum disactivation of micro-organisms, these discharge lamps present a series of disadvantages.

When using low pressure mercury burners, the disinfection arrangements occupy a rather large volume. The reason for this can be found in the small output of emitted radiation per centimeter of discharge length. In addition thereto the emitting maximum is at 254 nm, there is the further disadvantage that the effect of this radiation corresponds only to about 80% of that one in the wave length range of 260 to 280 nm.

Low pressure discharge lamps are susceptible to variations in temperature, as they are caused, for example, by air flowing past the discharge vessels, manifesting itself by a reduced emitting capacity.

Space-saving arrangements can be made by using high pressure mercury burners which, moreover, are less susceptible to variations of temperature. These, however, are subject to the disadvantage that only a small radiation portion is emitted in the wave length range of 260 to 280 nm, yet there appears radiation in the range of 400 to 450 nm causing a re-activation of the micro-organisms.

SUMMARY OF THE INVENTION

It is therefore the object of the invention to make available a discharge lamp eliminating the mentioned disadvantages and effecting a disactivation of micro-organisms, without the arrangements to be made for that purpose having to be large-sized, that the discharge lamp will not be susceptible to variations of temperature and that a re-activation of micro-organisms is prevented.

According to the invention, this problem is solved in that the discharge lamp is a metal halide discharge lamp, containing antimony as a metal and iodine as a halogen.

By the excitation of these elements in the discharge lamp a radiation is emitted, concentrating itself in the wave length range between 200 nm and 315 nm and of the total output yielded in this range is emitting 40%. In addition thereto, there is a maximum of the radiation output in the range between 260 and 280 nm, thus contributing to an optimum disactivation of micro-organisms.

The radiation emitted in the adjacent wave length range up to 700 nm being especially distinct by the high pressure mercury burners and in the range of 400 to 450 nm is attributing to the reactivation of micro-organisms, with the discharge lamp according to the invention does appear to a slight extent only and presents a radiation portion of not more than 6%.

Since the power output of the discharge lamp according to the invention per centimeter of the discharge length far exceeds that of the low pressure lamps, with the low pressure discharge lamp one would need discharge lengths being approx. 10 times longer as compared to the metal halide lamp charged with antimony and iodine, in order to obtain the same power output. Thereby it can be seen that disactivation arrangements with the lamp according to the invention turn out to be rather compact. Thus the lamps according to the invention can be arranged around glass sections transmissible to ultraviolet rays of aeration systems to operating theaters, in order to produce disinfected air without having to provide for expensive arrangements.

If the discharge lamps in the above mentioned disinfecting arrangements for air and fluids are replaced by the metal halide discharge lamp according to the invention, then it is obvious that thereby a more effective disinfaction of the air or fluids will result.

As the discharge lamp according to the invention, when in operation, presents temperatures of approx. 700° on the glass walls, contrary to the low pressure discharge lamps, the emitted radiation is hardly influenced by variations of temperature.

Although when using high pressure mercury burners, the disactivation devices are likewise of compact configuration, tests have shown that with the same power output, the efficiency of the discharge lamp according to the invention was twice as much.

The construction of the metal halide discharge lamp according to the invention corresponds to that of the known high pressure mercury lamp. In order to obtain a radiation output of at least 40% of the total radiation in the wave length range of 210 to 315 nm, it is charged with 0.049 mg to 0.057 mg iodine and 0.016 to 0.024 mg antimony per $cm^3$ of the burner volume. For a priming gas neon is used generating a pressure of approximately 40 mb in the burner. On operation of the discharge lamp, there exists a gradient of approximately 4.5 volts per cm of discharge length if neon is used as a charging gas. In order to make the radiation output in the desired region of the spectrum even more independent of variations in temperature with respect to the burner walls, xenon must be used for a priming gas.

In this case, the partial pressure should be between 250 mb and atmospheric pressure, preferably around 500 mb. The desired distribution and output of radiation is then obtained when the burner is charged with 0.070 mg to 0.110 mg iodine and 0.035 mg to 0.055 mg antimony per $cm^3$ of the burner volume, and when the gradient during operation of the burner is 5 volts to 6 volts, preferably around 5.5 volts per cm of discharge length.

BRIEF DESCRIPTION OF THE DRAWINGS

Further details, features and advantages of the invention will result from the following description of the drawing, wherein:

FIG. 1 shows a schematic construction of a metal halide discharge lamp according to the invention;

FIG. 2 shows a spectrum of the emitted radiation of the discharge lamp according to the invention;

DESCRIPTION OF THE PREFERRED EMBODIMENT

Figure 3:
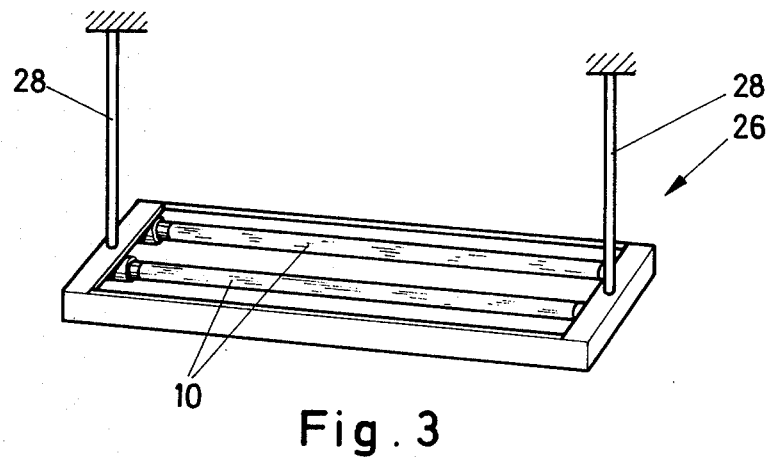
FIG. 3 is a schematic representation of a ceiling radiator with the discharge lamp according to the invention.

In FIG. 1 there is represented a metal halide discharge lamp 10 for the disactivation of micro organisms.

The discharge lamp 10 is composed of an evacuatable burner 12 of circular section, arranged in which are electrodes 14, 16. The electrodes 14, 16 can be configured as single or double wound tungsten filaments or in any other known form, and via electric feed lines 18, 20 being passed through the walls of the burner 12 made of glass transmissible to ultraviolet light, are connected to a supply point on operation of the discharge lamp 10. As an inert priming gas, neon or xenon is admitted to the burner 12.

When using neon, the pressure should be at 40 mb, when using xenon preferably around 500 mb. In addition to the priming inert gases the burner 12 contains technically pure iodine 22 and antimony 24, being in the form of powder or crystals. Per $cm^3$ of burner volume, typical values are 0.049 mg to 0.057 mg iodine 22 and 0.016 mg to 0.024 mg antimony 24 when using neon as a priming gas, and 0.070 mg to 0.110 mg iodine 22 and 0.035 mg to 0.055 mg antimony 24 when using xenon. For operation of the discharge lamp 10, the voltage at the electrodes 14, 16 is adjusted in such a manner that between the electrodes 14, 16 there is a gradient of approximately 4.5 volts with neon, and 5.5 volts with xenon per centimeter of the discharge length. In order to start the discharge, auxiliary electrodes (not shown) are arranged adjacent to the electrodes 14, 16. The electric switching of the discharge lamp 10 corresponds to that of a high pressure mercury lamp and, therefore, is not described in any further detail.

In FIG. 2 there is represented a spectral distribution of the radiation flow in relative units of the metal halide discharge lamp 10 according to the invention. The spectrum clearly shows a concentration of the emitted radiation in the wave length range between 210 nm and 330 nm, and a radiation intensity negligible thereto between 330 nm and 700 nm.

The emitted radiation of the metal halide discharge lamp 10 proves to be preferably suitable for the disactivation of gases and fluids. Thus in FIG. 3 there is shown schematically a ceiling radiator 26 with pendulums 28, being equipped with metal halide lamps 10, which is used for the air disinfection of rooms.

Figure 4:
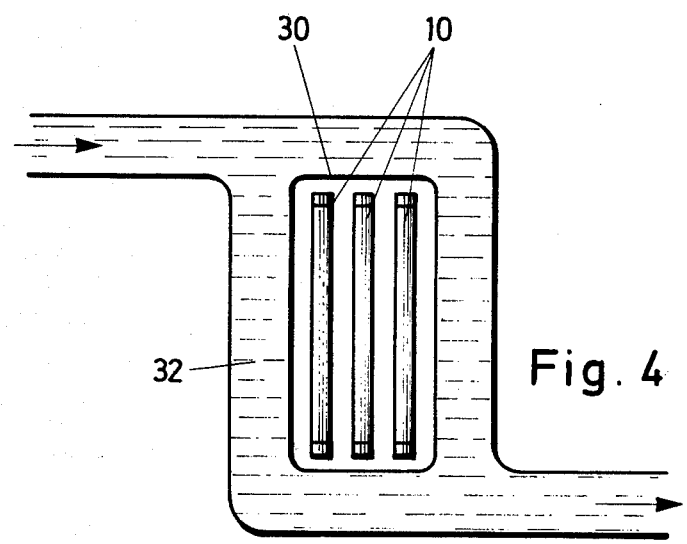
FIG. 4 is a schematic arrangement of a submerged lamp in a dip tank.

FIG. 4 schematically shows a submersible lamp 30 with metal halide lamps 10 in a dip tank 32 for the disinfection of water flowing through, for example.

Additionally the metal halide discharge lamp according to the invention can be used in the initially described arrangements.

I claim:

1. In a metal halide discharge lamp for the disactivation of micro organisms with an emitted radiation suitable for disactivation, the improvement comprising: said metal halide discharge lamp (10) contains antimony (24) as a metal and iodine (22) as a halogen.

2. A metal halide discharge lamp according to claim 1, characterized that the discharge lamp (10) contains neon as a charging gas with a partial pressure of approximately 40 mb, and in operation presents a gradient of about 4.5 volts per centimeter of the discharge length.

3. A metal halide discharge lamp according to claim 1, characterized thereby that in the discharge lamp (10) there are contained iodine in the range of 0.049 mg to 0.057 mg and antimony in the range of 0.016 mg to 0.024 mg per $cm^3$ of the burner volume.

4. A metal halide discharge lamp according to claim 1, characterized that the discharge lamp contains xenon as a charging gas with a partial pressure between 250 mb and atmospheric pressure, and in operation presents a gradient of 5 to 6 volts per cm of the discharge length.

5. A metal halide discharge lamp according to claim 4, characterized that the partial pressure of the charging gas xenon is approximately 500 mb.

6. A metal halide discharge lamp according to the claim 5, characterized that the discharge lamp on operation has a gradient of approximately 5.5 volts per cm of the discharge length.

7. A metal halide discharge lamp according to claim 1, characterized that the discharge lamp contains iodine in the range of 0.070 mg to 0.110 mg and antimony in the range of 0.035 mg to 0.055 mg per $cm^3$ of the burner volume.

8. A metal halide discharge lamp according to the claim 1, characterized that the discharge lamp (10) is arranged in ventilating air domes.

9. A metal halide discharge lamp according to the claim 1, characterized that the discharge lamp (10) is arranged in room disinfecting devices (26).

10. A metal halide discharge lamp according to the claim 1, characterized that the discharge lamp (10) as a submersible lamp (30) is arranged in a dip tank (32) for the disinfection of fluids.

* * * * *